(12) United States Patent
Gorrell et al.

(10) Patent No.: US 7,436,177 B2
(45) Date of Patent: Oct. 14, 2008

(54) SEM TEST APPARATUS

(75) Inventors: Jonathan Gorrell, Gainesville, FL (US); Mark Davidson, Florahome, FL (US); Jean Tokarz, Hawthorne, FL (US)

(73) Assignee: Virgin Islands Microsystems, Inc., Saint Thomas, VI (US)

( * ) Notice: Subject to any disclaimer, the term of this patent is extended or adjusted under 35 U.S.C. 154(b) by 334 days.

(21) Appl. No.: 11/418,081

(22) Filed: May 5, 2006

(65) Prior Publication Data

US 2007/0256472 A1 Nov. 8, 2007

(51) Int. Cl.
*H01J 25/50* (2006.01)

(52) U.S. Cl. .................... 324/317; 324/309; 315/39.51; 315/39.77

(58) Field of Classification Search .................. 324/317, 324/309; 315/39.51, 39.77
See application file for complete search history.

(56) References Cited

U.S. PATENT DOCUMENTS

| | | | |
|---|---|---|---|
| 1,948,384 A | 2/1934 | Lawrence | |
| 2,307,086 A | 1/1943 | Varian et al. | |
| 2,431,396 A | 11/1947 | Hansell | |
| 2,473,477 A | 6/1949 | Smith | |
| 2,634,372 A | 4/1953 | Salisbury | |
| 2,932,798 A | 4/1960 | Kerst et al. | |
| 3,571,642 A | 3/1971 | Westcott | |
| 3,761,828 A | 9/1973 | Pollard et al. | |
| 3,923,568 A | 12/1975 | Bersin | |
| 3,989,347 A | 11/1976 | Eschler | |
| 4,282,436 A | 8/1981 | Kapetanakos | |
| 4,482,779 A | 11/1984 | Anderson | |
| 4,727,550 A * | 2/1988 | Chang et al. | 372/2 |
| 4,740,973 A | 4/1988 | Madey | |
| 4,746,201 A | 5/1988 | Gould | |
| 4,829,527 A | 5/1989 | Wortman et al. | |
| 4,838,021 A | 6/1989 | Beattie | |
| 5,023,563 A | 6/1991 | Harvey et al. | |
| 5,157,000 A | 10/1992 | Elkind et al. | |
| 5,163,118 A | 11/1992 | Lorenzo et al. | |
| 5,185,073 A | 2/1993 | Bindra | |
| 5,199,918 A | 4/1993 | Kumar | |
| 5,262,656 A | 11/1993 | Blondeau et al. | |
| 5,263,043 A | 11/1993 | Walsh | |
| 5,268,693 A | 12/1993 | Walsh | |
| 5,268,788 A | 12/1993 | Fox et al. | |

(Continued)

FOREIGN PATENT DOCUMENTS

EP 0237559 B1 12/1991

(Continued)

OTHER PUBLICATIONS

J. C. Palais, "Fiber optic communications," Prentice Hall, New Jersey, 1998, pp. 156-158.

(Continued)

*Primary Examiner*—Kiet T Nguyen
(74) *Attorney, Agent, or Firm*—Davidson Berquist Jackson & Gowdey LLP

(57) ABSTRACT

Test apparatus for examining the operation and functioning of ultra-small resonant structures, and specifically using an SEM as the testing device and its electron beam as an exciting source of charged particles to cause the ultra-small resonant structures to resonate and produce EMR.

12 Claims, 3 Drawing Sheets

U.S. PATENT DOCUMENTS

| | | | |
|---|---|---|---|
| 5,302,240 A | 4/1994 | Hori et al. |
| 5,354,709 A | 10/1994 | Lorenzo et al. |
| 5,446,814 A | 8/1995 | Kuo et al. |
| 5,608,263 A | 3/1997 | Drayton et al. |
| 5,668,368 A | 9/1997 | Sakai et al. |
| 5,705,443 A | 1/1998 | Stauf et al. |
| 5,737,458 A | 4/1998 | Wojnarowski et al. |
| 5,744,919 A | 4/1998 | Mishin et al. |
| 5,757,009 A | 5/1998 | Walstrom |
| 5,767,013 A | 6/1998 | Park |
| 5,790,585 A * | 8/1998 | Walsh .................. 372/102 |
| 5,811,943 A | 9/1998 | Mishin et al. |
| 5,821,836 A | 10/1998 | Katehi et al. |
| 5,821,902 A | 10/1998 | Keen |
| 5,831,270 A | 11/1998 | Nakasuji |
| 5,847,745 A | 12/1998 | Shimizu et al. |
| 5,889,449 A | 3/1999 | Fiedziuszko |
| 5,902,489 A | 5/1999 | Yasuda et al. |
| 6,008,496 A | 12/1999 | Winefordner et al. |
| 6,040,625 A | 3/2000 | Ip |
| 6,060,833 A | 5/2000 | Velazco |
| 6,080,529 A | 6/2000 | Ye et al. |
| 6,195,199 B1 | 2/2001 | Yamada |
| 6,222,866 B1 | 4/2001 | Seko |
| 6,281,769 B1 | 8/2001 | Fiedziuszko |
| 6,297,511 B1 | 10/2001 | Syllaios et al. |
| 6,338,968 B1 | 1/2002 | Hefti |
| 6,370,306 B1 | 4/2002 | Sato et al. |
| 6,373,194 B1 | 4/2002 | Small |
| 6,376,258 B2 | 4/2002 | Hefti |
| 6,407,516 B1 | 6/2002 | Victor |
| 6,441,298 B1 | 8/2002 | Thio |
| 6,504,303 B2 | 1/2003 | Small |
| 6,545,425 B2 | 4/2003 | Victor |
| 6,577,040 B2 | 6/2003 | Nguyen |
| 6,603,915 B2 | 8/2003 | Glebov et al. |
| 6,624,916 B1 | 9/2003 | Green et al. |
| 6,636,653 B2 | 10/2003 | Miracky et al. |
| 6,642,907 B2 | 11/2003 | Hamada et al. |
| 6,738,176 B2 | 5/2004 | Rabinowitz et al. |
| 6,741,781 B2 | 5/2004 | Furuyama |
| 6,782,205 B2 | 8/2004 | Trisnadi et al. |
| 6,791,438 B2 | 9/2004 | Takahashi et al. |
| 6,829,286 B1 | 12/2004 | Guilfoyle et al. |
| 6,834,152 B2 | 12/2004 | Gunn et al. |
| 6,870,438 B1 | 3/2005 | Shino et al. |
| 6,885,262 B2 | 4/2005 | Nishimura et al. |
| 6,909,092 B2 | 6/2005 | Nagahama |
| 6,909,104 B1 | 6/2005 | Koops |
| 6,944,369 B2 | 9/2005 | Deliwala |
| 6,953,291 B2 | 10/2005 | Liu |
| 6,965,625 B2 | 11/2005 | Mross et al. |
| 6,995,406 B2 | 2/2006 | Tojo et al. |
| 7,010,183 B2 | 3/2006 | Estes et al. |
| 7,092,588 B2 | 8/2006 | Kondo |
| 7,092,603 B2 | 8/2006 | Glebov et al. |
| 7,122,978 B2 | 10/2006 | Nakanishi et al. |
| 7,177,515 B2 | 2/2007 | Estes et al. |
| 7,267,459 B2 | 9/2007 | Matheson |
| 7,267,461 B2 | 9/2007 | Kan et al. |
| 2001/0025925 A1 | 10/2001 | Abe et al. |
| 2002/0009723 A1 | 1/2002 | Hefti |
| 2002/0027481 A1 | 3/2002 | Fiedziuszko |
| 2002/0036264 A1 | 3/2002 | Nakasuji et al. |
| 2002/0053638 A1 | 5/2002 | Winkler et al. |
| 2002/0135665 A1 | 9/2002 | Gardner |
| 2003/0012925 A1 | 1/2003 | Gorrell |
| 2003/0016412 A1 | 1/2003 | Small |
| 2003/0016421 A1 | 1/2003 | Small |
| 2003/0034535 A1 | 2/2003 | Barenburu et al. |
| 2003/0155521 A1 | 8/2003 | Feuerbaum |
| 2003/0164947 A1 | 9/2003 | Vaupel |
| 2003/0179974 A1 | 9/2003 | Estes et al. |
| 2003/0206708 A1 | 11/2003 | Estes et al. |
| 2003/0214695 A1 | 11/2003 | Abramson et al. |
| 2004/0061053 A1 | 4/2004 | Taniguchi et al. |
| 2004/0108473 A1 | 6/2004 | Melnychuk et al. |
| 2004/0136715 A1 | 7/2004 | Kondo |
| 2004/0150991 A1 | 8/2004 | Ouderkirk et al. |
| 2004/0171272 A1 | 9/2004 | Jin et al. |
| 2004/0180244 A1 | 9/2004 | Tour et al. |
| 2004/0213375 A1 | 10/2004 | Bjorkholm et al. |
| 2004/0217297 A1 | 11/2004 | Moses et al. |
| 2004/0231996 A1 | 11/2004 | Webb |
| 2004/0240035 A1 | 12/2004 | Zhilkov |
| 2004/0264867 A1 | 12/2004 | Kondo |
| 2005/0023145 A1 | 2/2005 | Cohen et al. |
| 2005/0045821 A1 | 3/2005 | Noji et al. |
| 2005/0054151 A1 | 3/2005 | Lowther et al. |
| 2005/0067286 A1 | 3/2005 | Ahn et al. |
| 2005/0082469 A1 | 4/2005 | Carlo |
| 2005/0092929 A1 | 5/2005 | Schneiker |
| 2005/0105690 A1 | 5/2005 | Pau et al. |
| 2005/0145882 A1 | 7/2005 | Taylor et al. |
| 2005/0162104 A1 | 7/2005 | Victor et al. |
| 2005/0190637 A1 | 9/2005 | Ichimura et al. |
| 2005/0194258 A1 | 9/2005 | Cohen et al. |
| 2005/0201707 A1 | 9/2005 | Glebov et al. |
| 2005/0201717 A1 | 9/2005 | Matsumura et al. |
| 2005/0212503 A1 | 9/2005 | Deibele |
| 2005/0249451 A1 | 11/2005 | Baehr-Jones et al. |
| 2006/0007730 A1 | 1/2006 | Nakamura et al. |
| 2006/0018619 A1 | 1/2006 | Helffrich et al. |
| 2006/0035173 A1 | 2/2006 | Davidson et al. |
| 2006/0045418 A1 | 3/2006 | Cho et al. |
| 2006/0060782 A1 | 3/2006 | Khursheed |
| 2006/0062258 A1 | 3/2006 | Brau et al. |
| 2006/0159131 A1 | 7/2006 | Liu et al. |
| 2006/0164496 A1 | 7/2006 | Tokutake et al. |
| 2006/0208667 A1 | 9/2006 | Lys et al. |
| 2006/0216940 A1 | 9/2006 | Gorrell et al. |
| 2006/0243925 A1* | 11/2006 | Barker et al. ............ 250/504 R |
| 2006/0274922 A1 | 12/2006 | Ragsdale |
| 2007/0003781 A1 | 1/2007 | de Rochemont |
| 2007/0003765 A1 | 1/2007 | Hudson et al. |
| 2007/0075264 A1* | 4/2007 | Gorrell et al. ................ 250/400 |
| 2007/0086915 A1 | 4/2007 | LeBoeuf et al. |
| 2007/0116420 A1 | 5/2007 | Estes et al. |

FOREIGN PATENT DOCUMENTS

| | | |
|---|---|---|
| JP | 2004-32323 A | 1/2004 |
| WO | WO 87/01873 | 3/1987 |
| WO | WO 93/21663 A1 | 10/1993 |
| WO | WO 00/72413 | 11/2000 |
| WO | WO 02/25785 | 3/2002 |
| WO | WO 02/077607 | 10/2002 |
| WO | WO 2004/086560 | 10/2004 |
| WO | WO 2005/015143 A2 | 2/2005 |
| WO | WO 2006/042239 A2 | 4/2006 |
| WO | WO 2007/081389 | 7/2007 |
| WO | WO 2007/081390 | 7/2007 |
| WO | WO 2007/081391 | 7/2007 |

OTHER PUBLICATIONS

Search Report and Written Opinion mailed Dec. 20, 2007 in PCT Appln. No. PCT/US2006/022771.

Search Report and Written Opinion mailed Jan. 31, 2008 in PCT Appln. No. PCT/US2006/027427.

Search Report and Written Opinion mailed Jan. 8, 2008 in PCT Appln. No. PCT/US2006/028741.

Search Report and Written Opinion mailed Mar. 11, 2008 in PCT Appln. No. PCT/US2006/022679.

U.S. Appl. No. 11/418,082, filed May 5, 2006, Gorrell et al.

Lee Kwang-Cheol et al., "Deep X-Ray Mask with Integrated Actuator for 3D Microfabrication", Conference: Pacific Rim Workshop on Transducers and Micro/Nano Technologies, (Xiamen CHN), Jul. 22, 2002.

Markoff, John, "A Chip That Can Transfer Data Using Laser Light," The New York Times, Sep. 18, 2006.

S.M. Sze, "Semiconductor Devices Physics and Technology", 2nd Edition, Chapters 9 and 12, Copyright 1985, 2002.

Search Report and Written Opinion mailed Feb. 12, 2007 in PCT Appln. No. PCT/US2006/022682.

Search Report and Written Opinion mailed Feb. 20, 2007 in PCT Appln. No. PCT/US2006/022676.

Search Report and Written Opinion mailed Feb. 20, 2007 in PCT Appln. No. PCT/US2006/022772.

Search Report and Written Opinion mailed Feb. 20, 2007 in PCT Appln. No. PCT/US2006/022780.

Search Report and Written Opinion mailed Feb. 21, 2007 in PCT Appln. No. PCT/US2006/022684.

Search Report and Written Opinion mailed Jan. 17, 2007 in PCT Appln. No. PCT/US2006/022777.

Search Report and Written Opinion mailed Jan. 23, 2007 in PCT Appln. No. PCT/US2006/022781.

Search Report and Written Opinion mailed Mar. 7, 2007 in PCT Appln. No. PCT/US2006/022775.

Speller et al., "A Low-Noise MEMS Accelerometer for Unattended Ground Sensor Applications", Applied MEMS Inc., 12200 Parc Crest, Stafford, TX, USA 77477.

Thurn-Albrecht et al., "Ultrahigh-Density Nanowire Arrays Grown in Self-Assembled Diblock Copolymer Templates", Science 290. 5499, Dec. 15, 2000, pp. 2126-2129.

"Array of Nanoklystrons for Frequency Agility or Redundancy," NASA's Jet Propulsion Laboratory, NASA Tech Briefs, NPO-21033. 2001.

"Hardware Development Programs," Calabazas Creek Research, Inc. found at http://calcreek.com/hardware.html.

"Antenna Arrays." May 18, 2002. www.tpub.com/content/neets/14183/ccs/14183_159.htm.

"Diffraction Grating," hyperphysics.phy-astr.gsu.edu/hbase/phyopt/grating.html.

Alford, T.L. et al., "Advanced silver-based metallization patterning for ULSI applications," Microelectronic Engineering 55, 2001, pp. 383-388, Elsevier Science B.V.

Amato, Ivan, "An Everyman's Free-Election Laser?" Science, New Series, Oct. 16, 1992, p. 401, vol. 258 No. 5081, American Association for the Advancement of Science.

Andrews, H.L. et al., "Dispersion and Attenuation in a Smith-Purcell Free Electron Laser," The American Physical Society, Physical Review Special Topics—Accelerators and Beams 8 (2005), pp. 050703-1-050703-9.

Backe, H. et al. "Investigation of Far-Infrared Smith-Purcell Radiation at the 3.41 MeV Electron Injector Linac of the Mainz Microtron MAMI," Institut fur Kernphysik, Universitat Mainz, D-55099, Mainz Germany.

Bakhtyari, A. et al., "Horn Resonator Boosts Miniature Free-Electron Laser Power," Applied Physics Letters, May 12, 2003, pp. 3150-3152, vol. 82, No. 19, American Institute of Physics.

Bakhtyari, Dr. Arash, "Gain Mechanism in a Smith-Purcell MicroFEL," Abstract, Department of Physics and Astronomy, Dartmouth College.

Bhattacharjee, Sudeep et al., "Folded Waveguide Traveling-Wave Tube Sources for Terahertz Radiation." IEEE Transactions on Plasma Science, vol. 32. No. 3, Jun. 2004, pp. 1002-1014.

Booske, J.H. et al., "Microfabricated TWTs as High Power, Wideband Sources of THz Radiation".

Brau, C.A. et al., "Gain and Coherent Radiation from a Smith-Purcell Free Electron Laser," Proceedings of the 2004 FEL Conference, pp. 278-281.

Brownell, J.H. et al., "Improved µFEL Performance with Novel Resonator," Jan. 7, 2005, from website: www.frascati.enea.it/thz-bridge/workshop/presentations/Wednesday/We-07-Brownell.ppt.

Brownell, J.H. et al., "The Angular Distribution of the Power Produced by Smith-Purcell Radiation," J. Phys. D: Appl. Phys. 1997, pp. 2478-2481, vol. 30, IOP Publishing Ltd., United Kingdom.

Chuang, S.L. et al., "Enhancement of Smith-Purcell Radiation from a Grating with Surface-Plasmon Excitation," Journal of the Optical Society of America, Jun. 1984, pp. 672-676, vol. 1 No. 6, Optical Society of America.

Chuang, S.L. et al., "Smith-Purcell Radiation from a Charge Moving Above a Penetrable Grating," IEEE MTT-S Digest, 1983, pp. 405-406, IEEE.

Far-IR, Sub-MM & MM Detector Technology Workshop list of manuscripts, session 6 2002.

Feltz, W.F. et al., "Near-Continuous Profiling of Temperature, Moisture, and Atmospheric Stabilty Using the Atmospheric Emitted Radiance Interferometer (AERI)," Journal of Applied Meteorology, May 2003, vol. 42 No. 5, H.W. Wilson Company, pp. 584-597.

Freund, H. P. et al., "Linearized Field Theory of a Smith-Purcell Traveling Wave Tube," IEEE Transactions on Plasma Science, Jun. 2004, pp. 1015-1027, vol. 32 No. 3, IEEE.

Gallerano, G. P. et al., "Overview of Terahertz Radiation Sources," Proceedings of the 2004 FEL Conference, pp. 216-221.

Goldstein, M. et al., "Demonstration of a Micro Far-Infrared Smith-Purcell Emitter," Applied Physics Letters, Jul. 28, 1997, pp. 452-454, vol. 71 No. 4, American Institute of Physics.

Gover, A. et al., "Angular Radiation Pattern of Smith-Purcell Radiation," Journal of the Optical Society of America, Oct. 1984, pp. 723-728, vol. 1 No. 5, Optical Society of America.

Grishin, Yu. A. et al., "Pulsed Orotron—A New Microwave Source for Submillimeter Pulse High-Field Electron Paramagnetic Resonance Spectroscopy," Review of Scientific Instruments, Sep. 2004, pp. 2926-2936, vol. 75 No. 9, American Institute of Physics.

Ishizuka, H. et al., "Smith-Purcell Experiment Utilizing a Field-Emitter Array Cathode: Measurements of Radiation," Nuclear Instruments and Methods in Physics Research, 2001, pp. 593-598, A 475, Elsevier Science B.V.

Ishizuka, H. et al., "Smith-Purcell Radiation Experiment Using a Field-Emission Array Cathode," Nuclear Instruments and Methods in Physics Research, 2000, pp. 276-280, A 445, Elsevier Science B.V.

Ives, Lawrence et al., "Development of Backward Wave Oscillators for Terahertz Applications," Terahertz for Military and Security Applications, Proceedings of SPIE vol. 5070 (2003), pp. 71-82.

Ives, R. Lawrence, "IVEC Summary, Session 2, Sources I" 2002.

Jonietz, Erika, "Nano Antenna Gold nanospheres show path to all-optical computing," Technology Review, Dec. 2005/Jan. 2006, p. 32.

Joo, Youngcheol et al., "Air Cooling of IC Chip with Novel Microchannels Monolithically Formed on Chip Front Surface," Cooling and Thermal Design of Electronic Systems (HTD-vol. 319 & EEP-vol. 15), International Mechanical Engineering Congress and Exposition, San Francisco, CA Nov 1995 pp. 117-121.

Joo, Youngcheol et al., "Fabrication of Monolithic Microchannels for IC Chip Cooling," 1995, Mechanical, Aerospace and Nuclear Engineering Department, University of California at Los Angeles.

Jung, K.B. et al., "Patterning of Cu, Co, Fe, and Ag for magnetic nanostructures," J. Vac. Sci. Technol. A 15(3), May/Jun. 1997, pp. 1780-1784.

Kapp, Oscar H. et al., "Modification of a Scanning Electron Microscope to Produce Smith-Purcell Radiation," Review of Scientific Instruments, Nov. 2004, pp. 4732-4741, vol. 75 No. 11, American Institute of Physics.

Kiener, C. et al., "Investigation of the Mean Free Path of Hot Electrons in GaAs/AlGaAs Heterostructures," Semicond. Sci. Technol., 1994, pp. 193-197, vol. 9, IOP Publishing Ltd., United Kingdom.

Kim, Shang Hoon, "Quantum Mechanical Theory of Free-Electron Two-Quantum Stark Emission Driven by Transverse Motion," Journal of the Physical Society of Japan, Aug. 1993, vol. 62 No. 8, pp. 2528-2532.

Korbly, S.E. et al., "Progress on a Smith-Purcell Radiation Bunch Length Diagnostic," Plasma Science and Fusion Center, MIT, Cambridge, MA.

Kormann, T. et al., "A Photoelectron Source for the Study of Smith-Purcell Radiation".

Kube, G. et al., "Observation of Optical Smith-Purcell Radiation at an Electron Beam Energy of 855 MeV," Physical Review E, May 8, 2002, vol. 65, The American Physical Society, pp. 056501-1-056501-15.

Liu, Chuan Sheng, et al., "Stimulated Coherent Smith-Purcell Radiation from a Metallic Grating," IEEE Journal of Quantum Electronics, Oct. 1999, pp. 1386-1389, vol. 35, No. 10, IEEE.

Manohara, Harish et al., "Field Emission Testing of Carbon Nanotubes for THz Frequency Vacuum Microtube Sources." Abstract. Dec. 2003. from SPIEWeb.

Manohara, Harish M. et al., "Design and Fabrication of a THz Nanoklystron".

Manohara, Harish M. et al., "Design and Fabrication of a THz Nanoklystron" (www.sofia.usra.edu/det_workshop/ posters/session 3/3-43 manohara_poster.pdf), PowerPoint Presentation.

McDaniel, James C. et al., "Smith-Purcell Radiation in the High Conductivity and Plasma Frequency Limits," Applied Optics, Nov. 15, 1989, pp. 4924-4929, vol. 28 No. 22, Optical Society of America.

Meyer, Stephan, "Far IR, Sub-MM &MM Detector Technology Workshop Summary," Oct. 2002. (may date the Manohara documents).

Mokhoff, Nicolas, "Optical-speed light detector promises fast space talk," EETimes Online, Mar. 20, 2006, from website: www.eetimes.com/showArticle.jhtml?articleID=183701047.

Nguyen, Phucanh et al., "Novel technique to pattern silver using CF4 and CF4/O2 glow discharges," J.Vac. Sci. Technol. B 19(1), Jan./Feb. 2001, American Vacuum Society, pp. 158-165.

Nguyen, Phucanh et al., "Reactive ion etch of patterned and blanket silver thin films in Cl2/O2 and O2 glow discharges," J. Vac. Sci, Technol. B. 17 (5), Sep./Oct. 1999, American Vacuum Society, pp. 2204-2209.

Ohtaka, Kazou, "Smith-Purcell Radiation from Metallic and Dielectric Photonic Crystals," Center for Frontier Science, pp. 272-273, Chiba University, 1-33 Yayoi, Inage-ku, Chiba-shi, Japan.

Phototonics Research, "Surface-Plasmon-Enhanced Random Laser Demonstrated," Phototonics Spectra, Feb. 2005, pp. 112-113.

Platt, C.L. et al., "A New Resonator Design for Smith-Purcell Free Electron Lasers," 6Q19, p. 296.

Potylitsin, A.P., "Resonant Diffraction Radiation and Smith-Purcell Effect," (Abstract), arXiv: physics/9803043 v2 Apr. 13, 1998.

Potylitsyn, A.P., "Resonant Diffraction Radiation and Smith-Purcell Effect," Physics Letters A, Feb. 2, 1998, pp. 112-116, A 238, Elsevier Science B.V.

S. Hoogland et al., "A solution-processed 1.53 μm quantum dot laser with temperature-invariant emission wavelength," Optics Express, vol. 14, No. 8, Apr. 17, 2006, pp. 3273-3281.

Savilov, Andrey V., "Stimulated Wave Scattering in the Smith-Purcell FEL," IEEE Transactions on Plasma Science, Oct. 2001, pp. 820-823, vol. 29 No. 5, IEEE.

Schachter, Levi et al., "Smith-Purcell Oscillator in an Exponential Gain Regime," Journal of Applied Physics, Apr. 15, 1989, pp. 3267-3269, vol. 65 No. 8, American Institute of Physics.

Schachter, Levi, "Influence of the Guiding Magnetic Field on the Performance of a Smith-Purcell Amplifier Operating in the Weak Compton Regime," Journal of the Optical Society of America, May 1990, pp. 873-876, vol. 7 No. 5, Optical Society of America.

Schachter, Levi, "The Influence of the Guided Magnetic Field on the Performance of a Smith-Purcell Amplifier Operating in the Strong Compton Regime," Journal of Applied Physics, Apr. 15, 1990, pp. 3582-3592, vol. 67 No. 8, American Institute of Physics.

Shih, I. et al., "Experimental Investigations of Smith-Purcell Radiation," Journal of the Optical Society of America, Mar. 1990, pp. 351-356, vol. 7, No. 3, Optical Society of America.

Shih, I. et al., "Measurements of Smith-Purcell Radiation," Journal of the Optical Society of America, Mar. 1990, pp. 345-350, vol. 7 No. 3, Optical Society of America.

Swartz, J.C. et al., "THz-FIR Grating Coupled Radiation Source," Plasma Science, 1998, 1D02, p. 126.

Temkin, Richard, "Scanning with Ease Through the Far Infrared," Science, New Series, May 8, 1998, p. 854, vol. 280, No. 5365, American Association for the Advancement of Science.

Walsh, J.E., et al., 1999. From website: http://www.ieee.org/organizations/pubs/newsletters/leos/feb99/hot2.htm.

Wentworth, Stuart M. et al., "Far-Infrared Composite Microbolometers," IEEE MTT-S Digest, 1990, pp. 1309-1310.

Yamamoto, N. et al., "Photon Emission From Silver Particles Induced by a High-Energy Electron Beam," Physical Review B, Nov. 6, 2001, pp. 205419-1-205419-9, vol. 64, The American Physical Society.

Yokoo, K. et al., "Smith-Purcell Radiation at Optical Wavelength Using a Field-Emitter Array," Technical Digest of IVMC, 2003, pp. 77-78.

Zeng, Yuxiao et al., "Processing and encapsulation of silver patterns by using reactive ion etch and ammonia anneal," Materials Chemistry and Physics 66, 2000, pp. 77-82.

Search Report and Written Opinion mailed Aug. 24, 2007 in PCT Appln. No. PCT/US2006/022768.

Search Report and Written Opinion mailed Aug. 31, 2007 in PCT Appln. No. PCT/US2006/022680.

Search Report and Written Opinion mailed Jul. 16, 2007 in PCT Appln. No. PCT/US2006/022774.

Search Report and Written Opinion mailed Jul. 20, 2007 in PCT Appln. No. PCT/US2006/024216.

Search Report and Written Opinion mailed Jul. 26, 2007 in PCT Appln. No. PCT/US2006/022776.

Search Report and Written Opinion mailed Jun. 20, 2007 in PCT Appln. No. PCT/US2006/022779.

Search Report and Written Opinion mailed Sep. 12, 2007 in PCT Appln. No. PCT/US2006/022767.

Search Report and Written Opinion mailed Sep. 13, 2007 in PCT Appln. No. PCT/US2006/024217.

Search Report and Written Opinion mailed Sep. 17, 2007 in PCT Appln. No. PCT/US2006/022787.

Search Report and Written Opinion mailed Sep. 5, 2007 in PCT Appln. No. PCT/US2006/027428.

Search Report and Written Opinion mailed Sep. 17, 2007 in PCT Appln. No. PCT/US2006/022689.

International Search Report and Written Opinion mailed Nov. 23, 2007 in International Application No. PCT/US2006/022786.

Search Report and Written Opinion mailed Oct. 25, 2007 in PCT Appln. No. PCT/US2006/022687.

Search Report and Written Opinion mailed Oct. 26, 2007 in PCT Appln. No. PCT/US2006/022675.

Search Report and Written Opinion mailed Sep. 21, 2007 in PCT Appln. No. PCT/US2006/022688.

Search Report and Written Opinion mailed Sep. 25, 2007 in PCT appln. No. PCT/US2006/022681.

Search Report and Written Opinion mailed Sep. 26, 2007 in PCT Appln. No. PCT/US2006/024218.

* cited by examiner

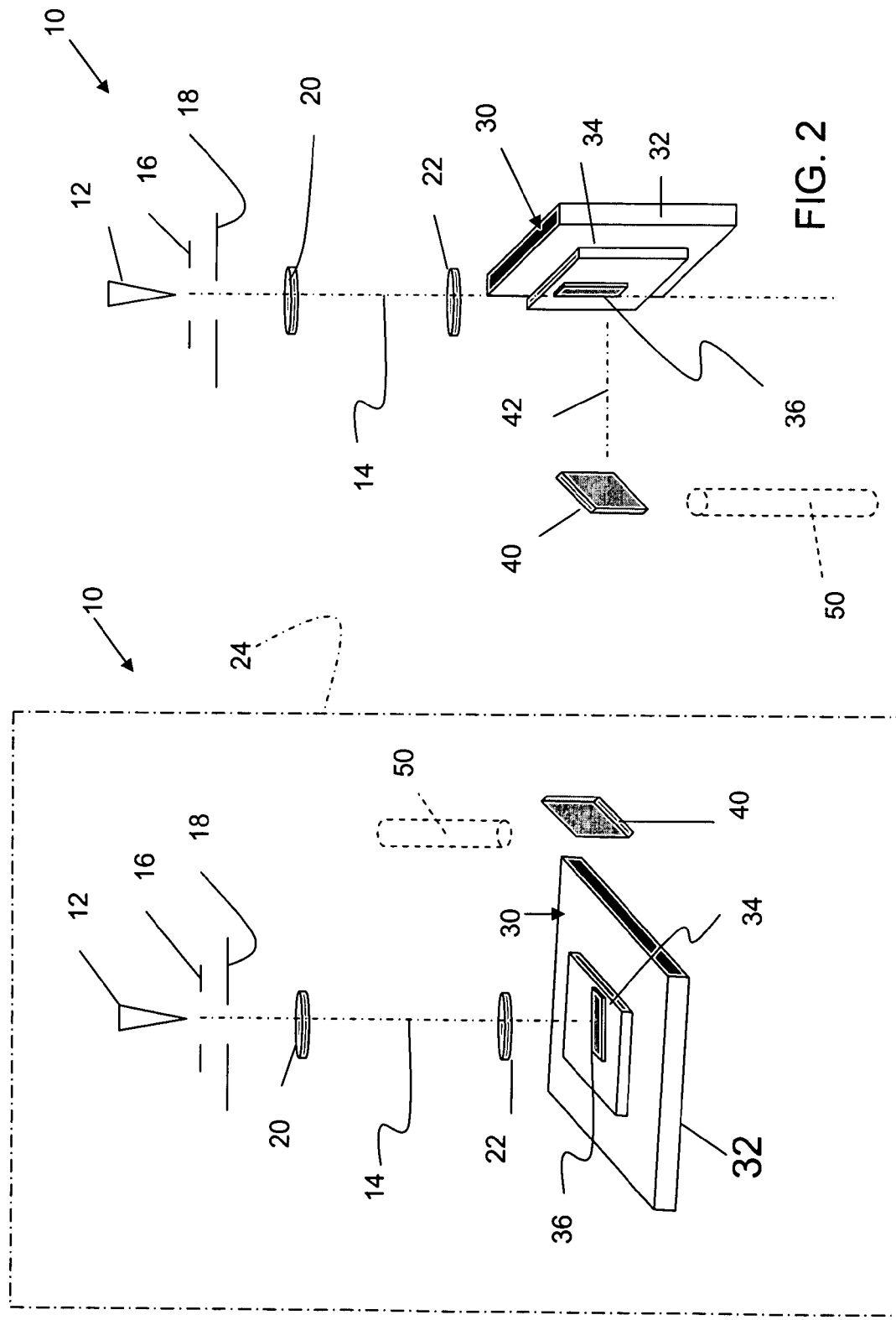

SEM TEST APPARATUS

COPYRIGHT NOTICE

A portion of the disclosure of this patent document contains material which is subject to copyright or mask work protection. The copyright or mask work owner has no objection to the facsimile reproduction by anyone of the patent document or the patent disclosure, as it appears in the Patent and Trademark Office patent file or records, but otherwise reserves all copyright or mask work rights whatsoever.

CROSS-REFERENCE TO CO-PENDING APPLICATIONS

The present invention is related to the following co-pending U.S. patent applications: (1) U.S. patent application Ser. No. 11/238,991, filed Sep. 30, 2005, entitled "Ultra-Small Resonating Charged Particle Beam Modulator"; (2) U.S. patent application Ser. No. 10/917,511, filed on Aug. 13, 2004, entitled "Patterning Thin Metal Film by Dry Reactive Ion Etching"; (3) U.S. application Ser. No. 11/203,407, filed on Aug. 15, 2005, entitled "Method Of Patterning Ultra-Small Structures"; (4) U.S. application Ser. No. 11/243,476, filed on Oct. 5, 2005, entitled "Structures And Methods For Coupling Energy From An Electromagnetic Wave"; (5) U.S. application Ser. No. 11/243,477, filed on Oct. 5, 2005, entitled "Electron beam induced Resonance"; (6) U.S. application Ser. No. 11/325,432, entitled "Resonant Structure-Based Display," filed on Jan. 5, 2006; (7) U.S. application Ser. No. 11/325,571, entitled "Switching Micro-Resonant Structures By Modulating A Beam Of Charged Particles," filed on Jan. 5, 2006; (8) U.S. application Ser. No. 11/325,534, entitled "Switching Micro-Resonant Structures Using At Least One Director," filed on Jan. 5, 2006; (9) U.S. application Ser. No. 11/350,812, entitled "Conductive Polymers for the Electroplating", filed on Feb. 10, 2006; (10) U.S. application Ser. No. 11/302,471, entitled "Coupled Nano-Resonating Energy Emitting Structures," filed on Dec. 14, 2005; and (11) U.S. application Ser. No. 11/325,448, entitled "Selectable Frequency Light Emitter", filed on Jan. 5, 2006, which are all commonly owned with the present application, the entire contents of each of which are incorporated herein by reference.

FIELD OF THE DISCLOSURE

This disclosure relates to the use and testing of ultra-small resonant structures, and arrays formed there from, together with the formation of associated structures located adjacent such ultra-small resonant structures, and specifically an approach for checking the operation of ultra-small resonant structures as they are excited by beams of charged particles directed there past within, for example, a high resolution, scanning electron microscope, a high resolution, field emission scanning electron microscope (FE-SEM) or an environmental scanning electron microscope (ESEM) (collectively referred to herein as an "SEM"), and light or other electromagnetic radiation (EMR) produced by the excited ultra-small resonant structures.

INTRODUCTION

Ultra-small structures encompass a range of structure sizes sometimes described as micro- or nano-sized. Objects with dimensions measured in ones, tens or hundreds of microns are described as micro-sized. Objects with dimensions measured in ones, tens or hundreds of nanometers or less are commonly designated nano-sized. Ultra-small hereinafter refers to structures and features ranging in size from hundreds of microns in size to ones of nanometers in size.

The devices of the present invention produce electromagnetic radiation (EMR), light or energy in a variety of spectrums by the excitation of ultra-small resonant structures. The resonant excitation in a device according to the invention is induced by electromagnetic interaction which is caused, e.g., by the passing of a charged particle beam in close proximity to the device. The charged particle beam can include ions (positive or negative), electrons, protons and the like. The beam may be produced by any source, including, e.g., without limitation an ion gun, a tungsten filament, a cathode, a planar vacuum triode, an electron-impact ionizer, a laser ionizer, a chemical ionizer, a thermal ionizer, an ion-impact ionizer. It is desirable to be able to quickly test the operation of ultra-small resonant structures formed on a substrate, to test such ultra-small resonant structures in a quick yet precise manner, and in apparatus that requires minimal set up. It is equally important that alignment of the beam of charged particles and the ultra-small resonant structures to be excited can be accomplished very precisely and under controlled and repeatable conditions.

Glossary: As used throughout this document:

The phrase "ultra-small resonant structure" shall mean any structure of any material, type or microscopic size that by its characteristics causes electrons to resonate at a frequency in excess of the microwave frequency.

The term "ultra-small" within the phrase "ultra-small resonant structure" shall mean microscopic structural dimensions and shall include so-called "micro" structures, "nano" structures, or any other very small structures that will produce resonance at frequencies in excess of microwave frequencies.

DESCRIPTION OF PRESENTLY PREFERRED EXAMPLES OF THE INVENTION

BRIEF DESCRIPTION OF FIGURES

The invention is better understood by reading the following detailed description with reference to the accompanying drawings in which:

FIG. 1 is a diagrammatic showing of a scanning electron microscope (SEM) based test apparatus;

FIG. 2 is a diagrammatic showing of an SEM where a nano-stage has been mounted and moved to orient an array of ultra-small resonant structures relative to a beam of charged particles within the SEM;

DESCRIPTION

Figure 3:
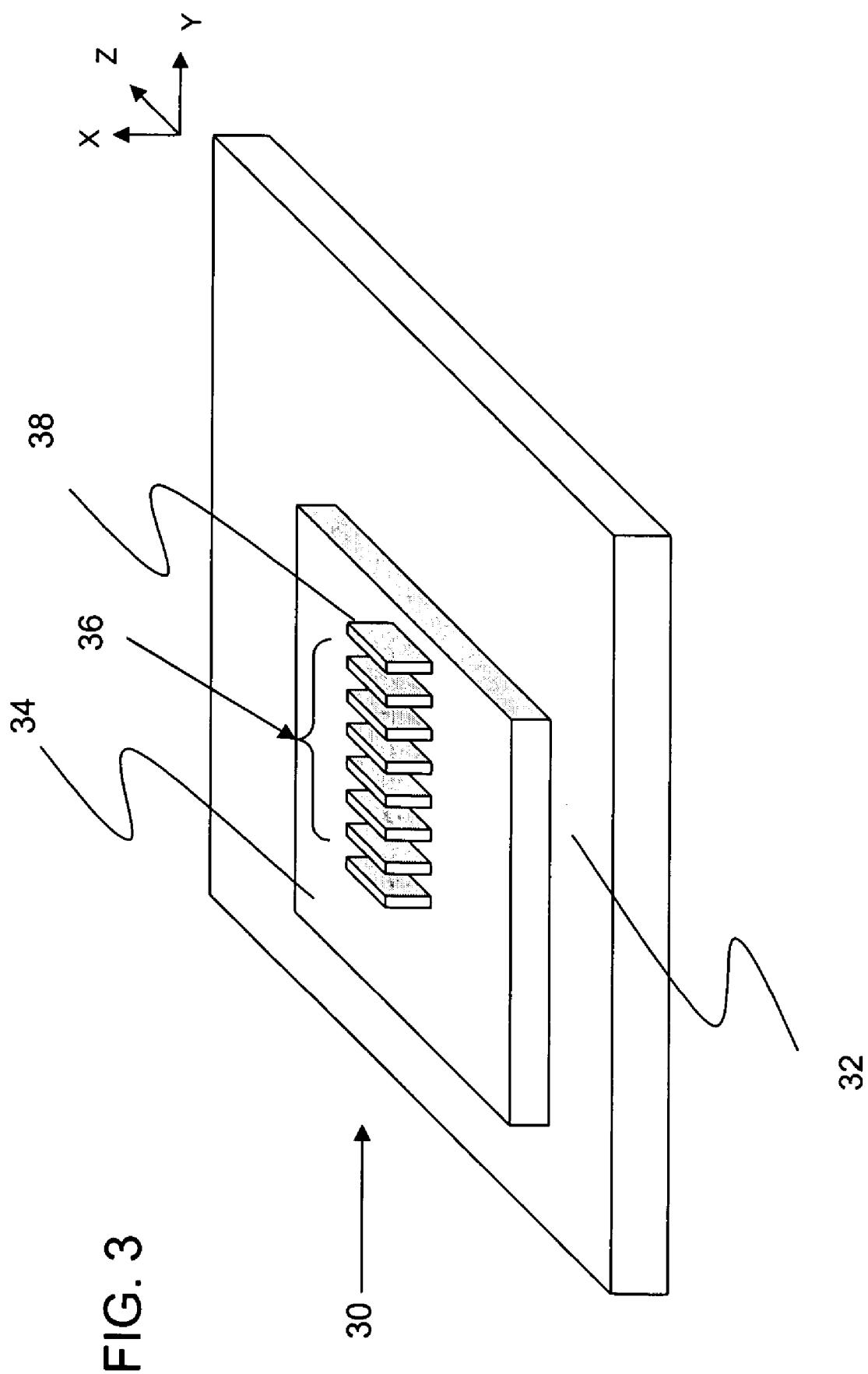
FIG. 3 shows an enlarged view of the nano-stage and its positions of movement.

Ultra-small resonating structures can be constructed with many types of materials. Examples of suitable fabrication materials include silver, copper, gold, and other high conductivity metals, and high temperature superconducting materials. The material may be opaque or semi-transparent. In the above-identified patent applications, ultra-small structures for producing electromagnetic radiation are disclosed, and methods of making the same. In at least one embodiment, the resonant structures of the present invention are made from at least one layer of metal (e.g., silver, gold, aluminum, platinum or copper or alloys made with such metals); however, multiple layers and non-metallic structures (e.g., carbon nanotubes and high temperature superconductors) can be utilized, as long as the structures are excited by the passage of a charged particle beam. The materials making up the resonant structures may be deposited on a substrate and then etched, electroplated, or otherwise processed to create a number of individual resonant elements. The material need not even be a contiguous layer, but can be a series of resonant elements individually present on a substrate. The materials making up the resonant elements can be produced by a variety of methods, such as by pulsed-plating, depositing or etching. Preferred methods for doing so are described in co-pending U.S. application Ser. No. 10/917,571 and Ser. No. 11/203,407, both of which were previously referenced above and incorporated herein by reference.

It is desirable to be able to have a convenient test apparatus to determine whether the ultra-small resonant structures work as expected and desired when excited by passing a beam of charged particles there past, as well as to look at and study the effects of how the out put of the ultra-small resonant structures may change as the exciting conditions change or as a result of modifications in their spacing, design, or shape, or as the type and power within the beam of charged particles is modified, as well as other aspects of the operation of such devices.

With reference to FIG. 1, a diagrammatic representation of a scanning electron microscope (SEM) 10 is set forth and includes a source 12 of a beam 14 of charged particles. Such a beam is usually focused or controlled to confine it by a suitable beam control 16, such as Wehnelt, or other similar beam control device that is part of the SEM, and an anode 18. An SEM will also include one or more condenser lenses 20 and an objective lens 22 to direct the beam within the microscope. Since SEM's are well known to those skilled in the art, further details thereof are not needed nor provided herein.

FIG. 1 also shows in phantom an outer housing 24 since the testing process will, as with SEM use, take place under vacuum conditions. Here again, the housing will differ with each model, type and manufacturer of SEM equipment thus requiring the housing to be represented only. This is not to be taken as a limiting factor with the present invention.

FIG. 1 also shows a stage to hold the sample being tested, and in particular a nano-stage for holding and positioning the array of ultra-small resonant structures. The nano-stage 30 includes a main stage 32 on which the substrate 34 is mounted and on which has been formed a light emitting device array 36. It should be understood that the light emitting device array 36 of ultra-small resonant structures should contain two or more ultra-small resonant structures 38, as shown in FIG. 3, it can be formed from a plurality of ultra-small resonant structures. In addition, the light emitting device array 36 could be comprised of several arrays of ultra-small resonant structures, and the substrate 36 could be a portion of a chip, an entire chip, or a portion of a substrate being used in the formation of ultra-small resonant structures that has been cut from a larger substrate. In FIG. 1 the stage has been placed in the SEM but has not yet been oriented.

FIG. 2 shows the nano-stage 30 as having been both rotated and tilted to orient the array 36 to be aligned with and preferably parallel with the beam 14. Nano-stage 30 has been designed to be movable in multiple directions, including at least the X, Y and Z directions, as shown by that symbol in FIG. 2. In addition, the nano-stage 30 is also tiltable and rotatable in multiple directions and degrees. Movement in the X direction in an SEM is normally in a range of about 0 to 100 mm, but only movement in the range of 0-100 nm is required in most instances for nano-stage 30. Movement in the Y and Z directions are usually in the range of 0-80 mm and 0-50 mm, respectively, but with the nano-stage 30, Y and Z movement in the ranges of 0-80 nm and 0-50 nm, respectively, should be sufficient. Tilting can be in the range of about −10° and +90°. Rotation is preferably 360°. It is possible to test these devices with nano-stage control of only two translation and one rotation axis but it is preferred to have three and two, respectively. It is preferred to have control over the movement of nano-stage 30 be either manual, via a joy stick, or by having incremental movement under the control of a software or computer program that can be either pre-set or controlled by a combination of manual and/or automatic inputs. Each of these movement parameters will be visible on digital readouts or other similar displays so that it is possible to monitor and vary each parameter as an independent entity or collectively.

While it is possible to use any substrate sample with an array of ultra-small resonant structures, it is preferred that the array be formed adjacent an edge of the substrate, or that the substrate be cut so that one cut edge be directly adjacent the cut edge. This makes the orientation of the substrate and the array on the nano-stage, that is from the position shown in FIG. 1 to that shown in FIG. 2 be an easier task. Alignment of the beam 14 so that it passes across the top or side of the ultra-small resonant structures 38 can be accomplished with the array 36 located more centrally on the substrate 32, but that alignment is made easier when the ultra-small resonant structures 38 begin close to one edge of the cut substrate 32.

Nano-stage 30 can be driven by a variety of motorized devices, but a pico-drive motorized stage is preferred. One example is model 8081, a motorized five-axis tilt aligner, manufactured by New Focus, that can be operated and/or controlled by computerized, manual or joy-stick created signal inputs. The stage can be driven by a suitable picomotor, and the stage itself can have the following operational parameters:

| Style | Five-Axis Tilt Aligner |
|---|---|
| Motorized Axes | 5 |
| Degrees of Freedom | X, Y, Z, $\theta_x$, $\theta_y$ |
| Linear Travel | X, Y, Z = 3 mm |
| Angular Travel | $\theta_x$, $\theta_y$ = 8° |
| Minimum Incremental Motion | X, Y, Z = <30 nm |
| Angular Resolution | $\theta_x$, $\theta_y$ = <0.7 µrad |
| Maximum Load | 5 lbs |

Once the array 36 is aligned as desired with the beam 14, and the ultra-small resonant structures 38 are excited, the ultra-small resonant structures will begin to resonate and produce out put energy, for example EMR or light in some spectrum. To monitor and maintain a running check on the operation of the array 36 and the individual ultra-small resonant structures 38, one or more detectors, spectrometers, or some similar device, including a focal plane array, to receive and transmit the produced energy is needed. Such a detector 40 is shown in FIGS. 1 and 2, and in FIG. 2 the out put energy is shown at 42. An optical detector 50, shown in dotted line in FIGS. 1 and 2, can be used in place of detector 40, or it can be used to receive the produced energy 42 and direct that to another device.

Figure 4:
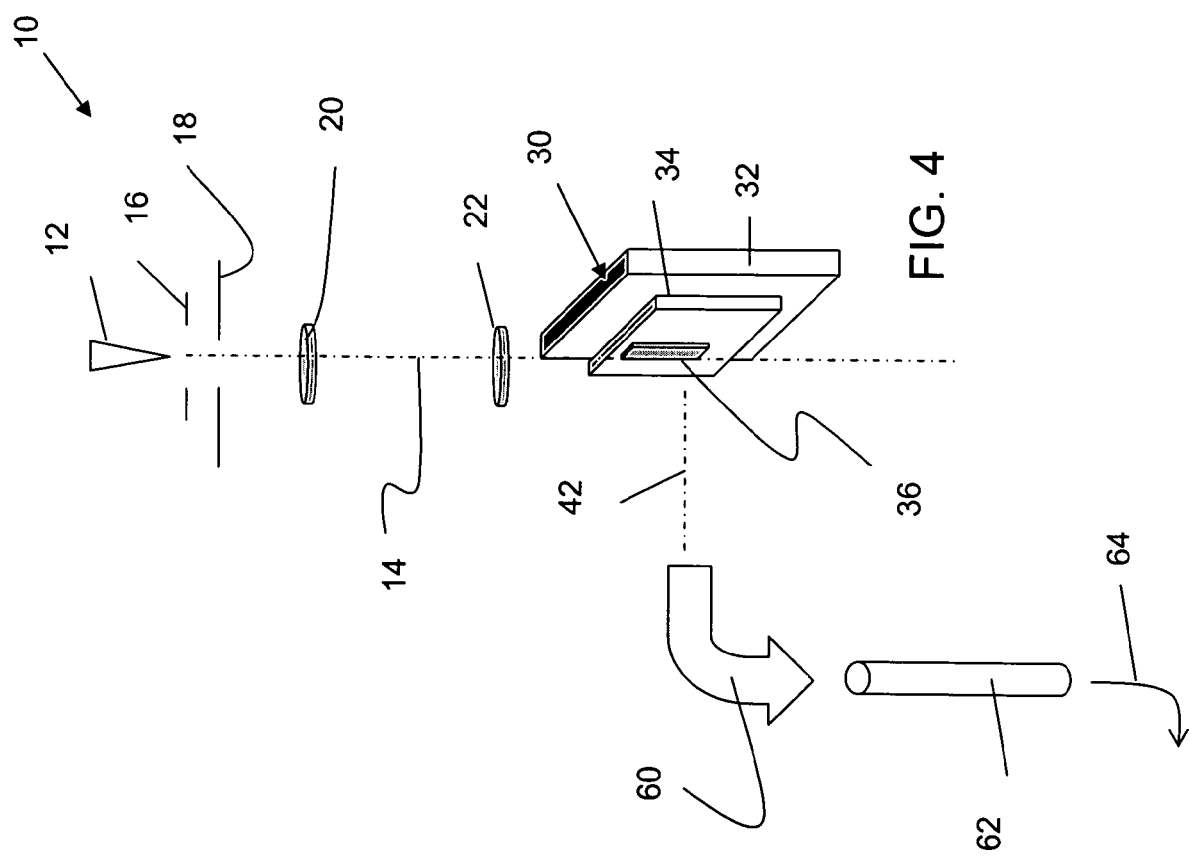
FIG. 4 shows another approach for detecting the EMR produced by the ultra-small resonant structures.

Another approach is shown in FIG. 4 where the produced energy 42 is received by an optical element 60 which can then send the received signal to a detector, such as shown at 50 in FIG. 2 that could be like one of those described above, or to another optical system 62 from which an output signal 64 is transmitted out of the microscope. With any of these detector concepts, the produced energy will ultimately be transmitted to a suitable display where the results can be seen, recorded or otherwise used and studied.

Using a SEM as a test apparatus is convenient since it has its own built in charged particle beam generator. Thus, it is only necessary to have as a sample an array of the ultra-small resonant structures on a substrate with the ability to then use the microscope's own beam to power or excite the ultra-small resonant structures. Determining the operating characteristics of any array of ultra-small resonant structures can be quickly checked, observed and modifications can be accomplished quickly and efficiently. Further, the nano-stage permits very small and precise changes in the orientation of the sample to be easily and quickly made, relative to the beam's path. This also permits multiple arrays on a sample substrate to be quickly checked by moving one and then another into alignment with the beam, or by aligning the substrate so that multiple arrays can be excited simultaneously by the beam of charged particles created within the SEM.

Devices according to the present invention are built from ultra-small resonant structures that have been formed on a suitable substrate. Thereafter, to perform testing of such devices, the substrate, or depending upon its size a portion of the substrate bearing the array to be tested can be cut out of the substrate, will be mounted on or to a stage that can be used on an electron microscope. It is preferred that the stage be movable through multiple planes and angles so that the alignment of the array within the electron microscope can be varied and changed. The stage is then placed in an electron microscope and the stage can then be positioned or oriented so that the path of the electron beam, or what ever type of beam of charged particles is being used, can be directed as desired along the array of ultra-small resonant structures. Once that stage position is established, the beam can be turned on, the array can be excited and suitable detectors, within a sight line of the energy out put from the array, such as EMR, can be received and signals generated corresponding to that out put EMR. Where movement of the beam is accomplished relative to the array during testing, for example by being deflected, where the stage itself is moved during testing, or where both the beam is deflected and the stage is moved, the detectors will receive the varying EMR being emitted in accordance with the relative movement between the array and the beam. This permits beam movement to be viewed, studied and experimented with and the results observed.

In addition, the operation of the ultra-small resonant structures frequently involves the movement or deflection of the beam of charged particles. Consequently, it is also desirable to be able to deflect the beam of charged particles coming from the source thereof with the SEM, to move or reposition the array on the stage during or as a part of the testing and exciting process, or both.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

We claim:

1. A test apparatus for examining the operation of ultra-small resonant structures comprising:
   an array of ultra-small resonant structures formed on a substrate;
   a SEM including a source of a beam of charged particles;
   a multi-positional stage mountable within the SEM and on which the array is mounted, the stage being movable in multiple directions relative to a path of a beam of charged particles produced by the source so that the array can be oriented relative to the beam and be excited thereby.

2. The test apparatus as in claim 1 wherein the positioning of the stage is controlled to position the array relative to the beam further comprises a source of control inputs.

3. The test apparatus as in claim 1 further including at least one detector for receiving energy produced by the array when excited by the beam and at least one display operatively connected to the detector for displaying the energy produced by the array.

4. The test apparatus as in claim 3 wherein the detector includes an optical pick-up assembly.

5. The test apparatus as in claim 3 wherein the detector comprises a focal plane array.

6. The test apparatus as in claim 1 further including a beam deflector to move the beam relative to the array.

7. The test apparatus as in claim 1 wherein the stage is movable prior to and during the generation of the beam.

8. The test apparatus as in claim 1 wherein the beam is movable relative to the array.

9. The test apparatus as in claim 1 wherein multiple arrays are provided on the substrate and the beam is oriented to excite the multiple arrays.

10. The test apparatus as in claim 1 wherein the substrate comprises a chip.

11. The test apparatus as in claim 1 wherein the SEM comprises a scanning electron microscope.

12. The test apparatus as in claim 1 wherein the SEM comprises a field emission scanning electron microscope.

* * * * *